(12) United States Patent
Tan

(10) Patent No.: US 11,331,188 B2
(45) Date of Patent: May 17, 2022

(54) ADJUSTABLE ARTIFICIAL CHORDAE TENDINEAE FIXING ASSEMBLY AND AN IMPLANTING METHOD THEREOF

(71) Applicant: Xiongjin Tan, Beijing (CN)

(72) Inventor: Xiongjin Tan, Beijing (CN)

( * ) Notice: Subject to any disclaimer, the term of this patent is extended or adjusted under 35 U.S.C. 154(b) by 33 days.

(21) Appl. No.: 16/649,147

(22) PCT Filed: Oct. 31, 2018

(86) PCT No.: PCT/CN2018/113008
§ 371 (c)(1),
(2) Date: Mar. 20, 2020

(87) PCT Pub. No.: WO2019/114448
PCT Pub. Date: Jun. 20, 2019

(65) Prior Publication Data
US 2020/0375740 A1    Dec. 3, 2020

(30) Foreign Application Priority Data

Dec. 14, 2017    (CN) .......................... 201711340665.7

(51) Int. Cl.
*A61F 2/24*        (2006.01)
*A61B 17/00*       (2006.01)
*A61B 17/34*       (2006.01)

(52) U.S. Cl.
CPC ........ *A61F 2/2457* (2013.01); *A61B 17/0057* (2013.01); *A61F 2/2466* (2013.01);
(Continued)

(58) Field of Classification Search
CPC ................. A61F 2/2457; A61F 2/2466; A61B 2017/00623; A61B 2017/00619;
(Continued)

(56) References Cited

U.S. PATENT DOCUMENTS 8,690,911 B2 * 4/2014 Miles ................. A61B 17/1215
606/213
2004/0102809 A1 * 5/2004 Anderson .......... A61B 17/0487
606/232

(Continued)

FOREIGN PATENT DOCUMENTS

CN    102038528 A    5/2011
CN    103220993 A    7/2013
(Continued)

*Primary Examiner* — Alexander J Orkin
(74) *Attorney, Agent, or Firm* — Bayramoglu Law Offices LLC

(57) ABSTRACT

An adjustable artificial chordae tendineae fixing assembly includes an occlusion device and an adjusting rod which are both a hollow structure allowing the artificial chordae tendineae to pass through. The occlusion device is configured to be clamped on the interventricular septum. The occlusion device is provided with a switch adjusting device which controls the artificial chordae tendineae to move and to be fixed. The adjusting rod is connected to the occlusion device, and is capable of repeatedly adjusting the switch adjusting device on the occlusion device. The artificial chordae tendineae fixing assembly can fix the artificial chordae tendineae on the interventricular septum, and can also overcome the problem of unsuitable length of the artificial chordae tendineae in most of patients after the procedure due to cardiac changes. The artificial chordae tendineae is retained at the skin puncture point for a short time.

4 Claims, 10 Drawing Sheets

(52) U.S. Cl.
CPC . *A61B 17/3468* (2013.01); *A61B 2017/00592* (2013.01); *A61B 2017/00623* (2013.01); *A61F 2210/0014* (2013.01); *A61F 2220/0008* (2013.01)

(58) Field of Classification Search
CPC .... A61B 2017/0454; A61B 2017/0451; A61B 2017/00592
See application file for complete search history.

(56) References Cited

U.S. PATENT DOCUMENTS

| | | | | |
|---|---|---|---|---|
| 2006/0106279 | A1* | 5/2006 | Machold | A61B 17/00234 600/37 |
| 2006/0122647 | A1* | 6/2006 | Callaghan | A61B 17/0057 606/213 |
| 2006/0252984 | A1* | 11/2006 | Rahdert | A61B 17/0401 600/37 |
| 2007/0088388 | A1* | 4/2007 | Opolski | A61B 17/0057 606/213 |
| 2007/0213582 | A1* | 9/2007 | Zollinger | A61B 17/0487 600/37 |
| 2007/0265658 | A1* | 11/2007 | Nelson | A61F 2/2487 606/213 |
| 2013/0035757 | A1* | 2/2013 | Zentgraf | A61B 17/0467 623/2.1 |
| 2013/0261663 | A1* | 10/2013 | Bittenson | A61B 17/0401 606/232 |
| 2015/0057705 | A1* | 2/2015 | Vidlund | A61B 17/0057 606/228 |
| 2015/0223934 | A1* | 8/2015 | Vidlund | A61F 2/2412 623/2.11 |
| 2015/0272559 | A1 | 10/2015 | Rowe et al. | |
| 2018/0098772 | A1* | 4/2018 | Goldshtein | A61B 17/0057 |

FOREIGN PATENT DOCUMENTS

| | | |
|---|---|---|
| CN | 106163609 A | 11/2016 |
| CN | 107126265 A | 9/2017 |
| CN | 108065970 A | 5/2018 |

* cited by examiner the puncture sheath catheter passes through the interventricular septum along a guide wire Releasing the occlusion device on the interventricular septum

ADJUSTABLE ARTIFICIAL CHORDAE TENDINEAE FIXING ASSEMBLY AND AN IMPLANTING METHOD THEREOF

CROSS REFERENCE TO THE RELATED APPLICATIONS

This application is the national phase entry of International Application No. PCT/CN2018/113008, filed on Oct. 31, 2018, which is based upon and claims priority to Chinese Patent Application No. 201711340665.7, filed on Dec. 14, 2017, the entire contents of which are incorporated herein by reference.

TECHNICAL FIELD

The present disclosure belongs to the field of biomedical instruments, and specifically relates to an adjustable artificial chordae tendineae fixing assembly and an implanting method thereof.

BACKGROUND

At present, mitral regurgitation is one of the most common valvular diseases. It is mainly caused by mitral annulus dilatation, chordae tendineae insufficiency, myxomatous degeneration of the mitral valve, mitral prolapses, rheumatic valvular diseases, ischemic diseases. The open mitral valvuloplasty and the prosthetic replacement are the most effective methods for the treatment of mitral regurgitation. However, this surgery needs technical support of cardiopulmonary bypass and thus produces a great surgical trauma to the human body, which leads to severe postoperative complications and extremely high mortality from senile patients and patients with more complications.

Hence, in recent years, medical staff and researchers in various countries have dedicated efforts to exploring percutaneous mitral repair techniques. The interventional treatment methods now used include mitral annuloplasty, negative pressure suction suture and MitraClip, among which the MitraClip shows the most reliable treatment outcome. In the MitraClip, an implantable clip is delivered to a vicinity of the mitral by puncturing the atrial septum, and free margins of the anterior leaflet and the posterior leaflet are clamped to allow the leaflets to fit well at the end of systole in order to reduce the mitral regurgitation. However, the chordae tendineae cannot be implanted by this medical instrument, which performs a non-physiological repair.

The repair method of implanting the artificial chordae tendineae has shortcomings as well. Implanting the artificial chordae tendineae on the is close to the physiological state and usually is performed through the transapical approach, which produces a great surgical trauma and a high risk. Alternatively, the percutaneous approach can produce a safer minimally invasive treatment outcome, but how to fix the artificial chordae tendineae remains an urgent problem to be solved with the percutaneous approach. Moreover, once the artificial chordae tendineae is fixed, the length of the chordae tendineae cannot be adjusted anew. As the cardiac volume of the patient changes or the patient is out of anesthesia, the length of the artificial chordae tendineae needs to be adjusted accordingly. Otherwise, an abnormality of the cardiac occurs and leads to a failure of the procedure.

SUMMARY

In order to overcome the above-mentioned issues, the present disclosure provides a fixing assembly capable of repeatedly adjusting the length of the artificial chordae tendineae to fix the artificial chordae tendineae on the interventricular septum by an occlusion device.

The technical solutions of the present disclosure are as follows:

An adjustable artificial chordae tendineae fixing assembly includes an occlusion device and an adjusting rod. The occlusion device includes a first occlusion disc, a waist portion and a second occlusion disc. The middle of the first occlusion disc, the waist portion and the second occlusion disc of the occlusion device is provided with a penetrating passage allowing an artificial chordae tendineae to pass there through. A adjusting device is arranged at the opening of the penetrating passage of the first occlusion disc. The protruding portion on the outer side of the adjusting device is arranged outside the first occlusion disc. A locking assembly and a plurality of friction plates on the inner side of the adjusting device extend inside the opening of the penetrating passage. The plurality of friction plates are connected to the valve, and the number of the plurality of friction plates is at least two. The plurality of friction plates are controlled to be opened or closed by rotating the valve, so as to control the penetrating passage to be opened or closed. The occlusion device is an elastic mesh structure capable of producing an elastic deformation.

The adjusting rod is a hollow rod-shaped structure allowing the artificial chordae tendineae to pass there through. Two clamping jaws are arranged at the head of the adjusting rod, and the two clamping jaws are connected to a handle at the tail of the adjusting rod by a spring. The two clamping jaws are controlled to be opened and closed by pressing the handle at the tail of the adjusting rod. The two clamping jaws can be clamped on the protruding portion of the adjusting device to be connected to the occlusion device.

Further, a protrusion is arranged on the inner side of each of the two clamping jaws of the adjusting rod. A groove is arranged at the protruding portion of the adjusting device, and the protrusion is engaged with the groove when the adjusting rod is connected to the occlusion device.

Further, the protrusion in each of the two clamping jaws is provided with a first magnet, and the groove of the adjusting device is provided with a second magnet, wherein the polarity of the first magnet is opposite to the polarity of the second magnet. The two clamping jaws of the adjusting rod are tightly clamped on the protruding portion of the adjusting device of the occlusion device by a magnetic attraction of the protrusion and the groove.

Further, the locking assembly of the adjusting device is a threaded structure including a core and a ring. The core is connected to the plurality of friction plates. A thread is arranged on the outer side of the core, and a thread is arranged on the inner side of the ring. When the adjusting device is closed, the ring is screwed to be tightened, the core is tightened inward, and the gap between the plurality of friction plates is closed. When the adjusting device is opened, the ring is screwed to be loosened, the core restores, and the gap between the plurality of friction plates is opened.

Further, the occlusion device is woven from a nickel-titanium alloy wire, the diameter of the waist portion is 3 to 10 mm, the height of the waist portion is 2 to 20 mm, and the diameter of the first occlusion disc and the diameter of the second occlusion disc are both 7 to 28 mm.

Further, the diameter of the waist portion is 6 mm, the height of the waist portion is 8 mm, and the diameter of the first occlusion disc and the diameter of the second occlusion disc are both 10 mm.

An implanting method for the artificial chordae tendineae fixing assembly includes the following steps:

step 1, penetrating an interventricular septum by a puncture sheath catheter; inserting the artificial chordae tendineae into a free margin of a diseased mitral leaflet through the perforation of the interventricular septum; and pulling out the tail of the artificial chordae tendineae through the tail of the puncture sheath catheter;

step 2, connecting the adjusting rod to the adjusting device of the occlusion device; rotating the adjusting rod to open the plurality of friction plates of the adjusting device; wherein the artificial chordae tendineae penetrates into the occlusion device and the adjusting rod by using a traction pin, enters the penetrating passage from one side of the second occlusion disc, and is pulled out from the tail of the adjusting rod;

step 3, delivering the occlusion device and the adjusting rod along the puncture sheath catheter; releasing the second occlusion disc of the occlusion device on the left ventricular side of the interventricular septum; placing the waist portion of the occlusion device in the perforation of the interventricular septum; releasing the first occlusion disc of the occlusion device on the right ventricular side of the interventricular septum; clamping the occlusion device on the interventricular septum; pushing and pulling the artificial chordae tendineae outside the tail of the adjusting rod to adjust the length of the artificial chordae tendineae; and closing the plurality of friction plates of the adjusting device to fix the artificial chordae tendineae;

step 4, pressing the handle at the tail of the adjusting rod to open the two clamping jaws at the head of the adjusting rod; releasing the occlusion device; withdrawing the adjusting rod; and retaining the artificial chordae tendineae outside a sheath catheter at a jugular venipuncture;

step 5, delivering the thread trimmer along the tail of the artificial chordae tendineae; triggering the handle at the tail of the thread trimmer to cut off the artificial chordae tendineae after the thread trimmer reaches the occlusion device; withdrawing the thread trimmer; and performing hemostasis by a compression.

Further, step 4a is between step 4 and step 5, including: inserting the artificial chordae tendineae into the adjusting rod when the length of the artificial chordae tendineae is unsuitable since anesthesia ends, or a cardiac volume changes; delivering the adjusting rod to the outer side of the first occlusion disc along the artificial chordae tendineae; pressing the handle at the tail of the adjusting rod to clamp the two clamping jaws of the adjusting rod outside the protruding portion of the adjusting device with the aid of the chordae tendineae and magnetism; rotating the adjusting device to allow the plurality of friction plates to open the gap after the two clamping jaws are securely clamped; loosening the artificial chordae tendineae to readjust the length of the artificial chordae tendineae; rotating the adjusting rod to close the plurality of friction plates of the adjusting device; fixing the artificial chordae tendineae; separating the adjusting rod from the occlusion device; and withdrawing the adjusting rod from the body.

Further, the thread trimmer is a rod-shaped structure, the thread trimmer includes a thread trimming end and a handle end at two ends thereof, respectively. The thread trimming end is provided with a groove and a blade capable of moving up and down along the groove. The handle end is provided with a push button, wherein the push button is connected to the blade inside the thread trimmer, and the blade is controlled to move by the push button.

The present disclosure has the following advantages by using the above-mentioned technical solution:

1. In the present disclosure, the artificial chordae tendineae is fixed on the interventricular septum by the occlusion device of the artificial chordae tendineae fixing assembly, which can occlude the perforation left by the puncture sheath catheter, and can also fix the artificial chordae tendineae.

2. The occlusion device is controlled to be opened and closed by the adjusting device of the occlusion device of the present disclosure. The artificial tendon fixing assembly can effectively fix the artificial chordae tendineae when the friction plates are closed, and can allow the artificial chordae tendineae to move in the occlusion device when the friction plates are opened, which facilitates an adjustment of the length of the artificial chordae tendineae.

3. In the present disclosure, the problem of unsuitable length of the artificial chordae tendineae due to cardiac changes occurring in most of patients after the procedure can be overcome by using the artificial chordae tendineae fixing assembly. The artificial chordae tendineae is retained at the skin puncture point for a short time. The length of the artificial chordae tendineae is adjusted again by using the artificial chordae tendineae fixing assembly according to a cardiac change of the patient in an early postoperative period, so as to realize the function of repeatedly adjusting the artificial chordae tendineae.

4. According to the artificial chordae tendineae fixing assembly of the present disclosure, the protrusion on the clamping jaw is engaged with the groove on the outer side of the adjusting device of the occlusion device to increase the clamping force. In addition, the protrusion and the groove are provided with magnets having opposite polarities, so that the adjusting rod can be quickly connected to the occlusion device when entering the body again, thereby improving procedural efficiency.

wherein, 1—occlusion device, 11—first occlusion disc, 12—waist portion, 13—second occlusion disc, 2—adjusting device, 21—protruding portion, 211—groove, 22—locking assembly, 23—friction plate, 24—core, 25—ring, 3—adjusting rod, 31—clamping jaw, 311—protrusion, 32—handle, 33—spring, 34—first magnet, 35—second magnet, 4—thread trimmer, 41—blade, 42—push button, 5—traction pin.

DETAILED DESCRIPTION OF THE EMBODIMENTS

In order to clearly describe the objectives, technical solutions, and advantages of the present disclosure, the present disclosure will be further described in detail hereinafter with reference to the drawings and embodiments. It should be understood that the structural diagrams and specific embodiments described herein are only intended to illustrate the present disclosure rather than limiting the present disclosure.

Embodiment 1

Figure 1:
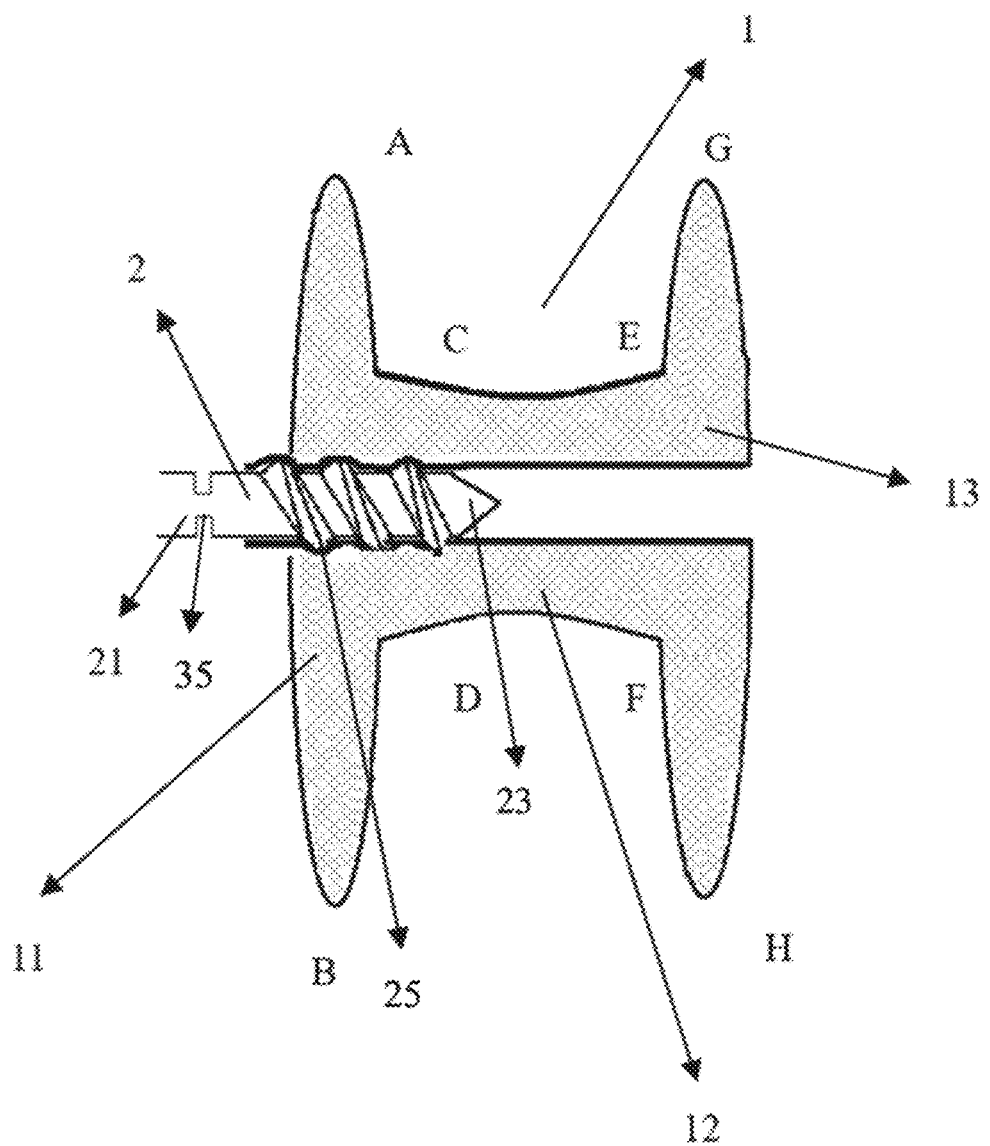
FIG. 1 is a structural schematic diagram of the occlusion device of the present disclosure.
Figure 2:
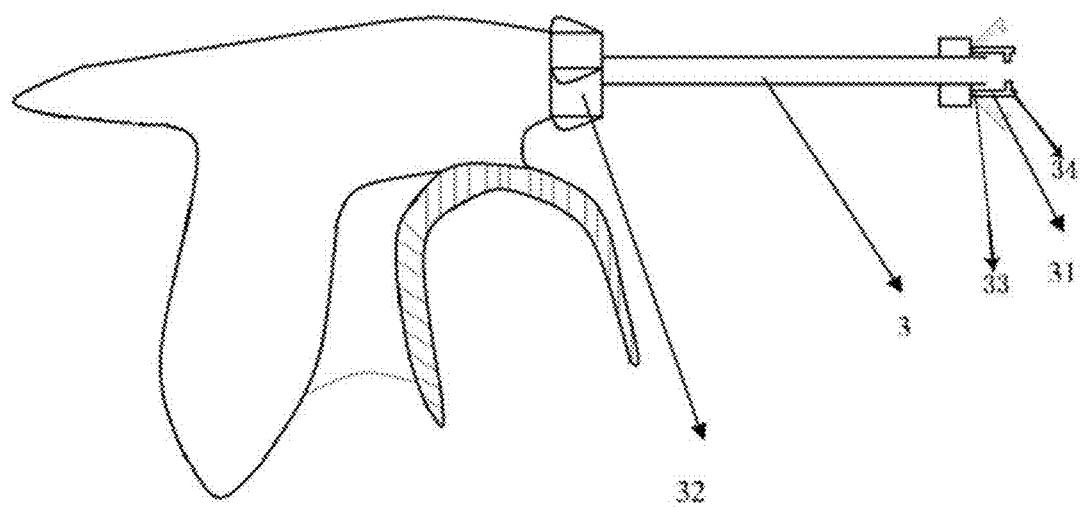
FIG. 2 is a structural schematic diagram of the adjusting rod of the present disclosure.

As shown in FIGS. 1 and 2, the present disclosure provides an adjustable artificial chordae tendineae fixing assembly, including the occlusion device 1 and the adjusting rod 3. The occlusion device 1 includes the first occlusion disc 11, the waist portion 12 and the second occlusion disc 13. The middle of the first occlusion disc 11, the waist portion 12 and the second occlusion disc 13 of the occlusion device 1 is provided with a penetrating passage allowing the artificial chordae tendineae to pass there through. The occlusion device 1 is an elastic mesh structure capable of producing an elastic deformation. The occlusion device can be compressed and tightened in the puncture sheath catheter. When the occlusion device 1 is released at the perforation of the interventricular septum, the perforation of the interventricular septum is filled with the waist portion 12 of the occlusion device 1, the first occlusion disc 11 and the second occlusion disc 13 are tightened from the left side to the middle and from the right side to the middle, respectively, and clamped and fixed on the interventricular septum.

The occlusion device 1 is woven from a nickel-titanium alloy wire. The diameter CD of the waist portion 12 is 3 to 10 mm, preferably 6 mm. The height CE of the waist portion 12 is 2 to 20 mm, preferably 8 mm. The diameter AB of the first occlusion disc 11 and the diameter GH of the second occlusion disc 13 are both 7 to 28 mm, and preferably 10 mm.

The adjusting device 2 is arranged at the opening of the penetrating passage of the first occlusion disc 11. The protruding portion 21 on the outer side of the adjusting device 2 is arranged outside the first occlusion disc 11. The locking assembly 22 and the plurality of friction plates 23 on the inner side of the adjusting device extend inside the opening of the penetrating passage. The plurality of friction plates 23 are connected to the locking assembly 22. The plurality of friction plates 23 are controlled to opened and closed by rotating the locking assembly 22, so as to control the penetrating passage of the first occlusion disc 11 to be opened and closed. The plurality of friction plates 23 can clamp the artificial chordae tendineae after being closed, to prevent a movement of the artificial chordae tendineae. The number of the plurality of friction plates 23 is at least two. The number of the plurality of friction plates 23 is not limited in the present disclosure, and thus can be even more according to different clamping forces required by the artificial chordae tendineae. For example, the number of the plurality of friction plates 23 is five, and the plurality of friction plates 23 are closed to form a "petal" shape, which enhances the clamping force on the artificial chordae tendineae.

The adjusting rod 3 is a hollow rod-shaped structure allowing the artificial chordae tendineae to pass through. Two clamping jaws 31 are arranged at the head of the adjusting rod 3, and the two clamping jaws 31 are connected to the handle 32 at the tail of the adjusting rod by a spring piece 33. The two clamping jaws 31 are controlled to be opened and closed by pressing the handle 32. The two clamping jaws 31 can be clamped on the protruding portion 21 of the adjusting device 2 to be connected to the occlusion device 1.

In the present disclosure, the locking assembly 22 of the adjusting device 2 is a threaded structure including a core 24 and a ring 25, as shown in FIG. 1. The core 24 is connected to the plurality of friction plates 23. A thread is arranged on the outer side of the core 24, and a thread is arranged on the inner side of the ring 25. When the adjusting device 2 is closed, the ring 25 is screwed to be tightened, the core 24 is tightened inward, and the gap between the plurality of friction plates 23 is closed. When the adjusting device 2 is opened, the ring 25 is screwed to be loosened, the core 24 restores, and the gap between the plurality of friction plates 23 is opened.

After the adjusting rod 3 is connected to the occlusion device, the ring 25 of the of the adjusting device 2 is rotated by clockwise rotating the adjusting rod 3 so that the ring 25 of the locking assembly 22 is rotated to reach the core 24 of the occlusion device 1; the core 24 is tightened, the friction plates 23 are closed to clamp the artificial chordae tendineae, so as to limit the movement of the artificial chordae tendineae. The ring 25 is rotated outward by rotating the adjusting rod 3 counterclockwise, the core 24 restores, and the plurality of friction plates 23 that are closed to one another are loosened to form a gap so that the artificial chordae tendineae can move in the gap.

Embodiment 2

Figure 3:
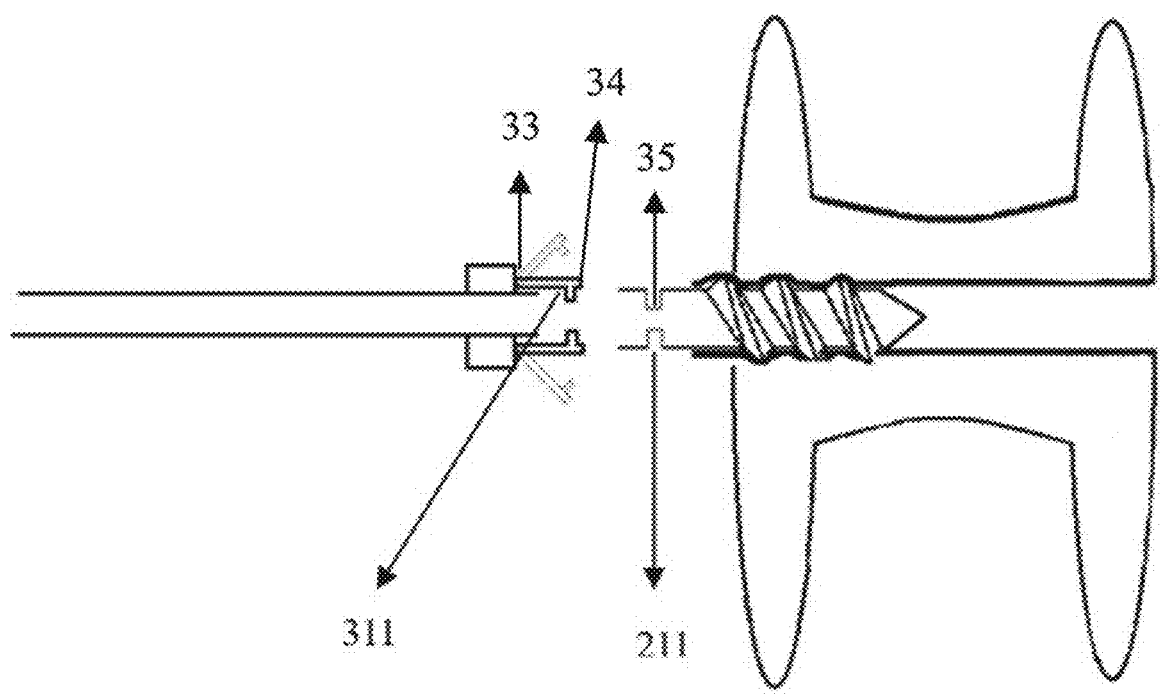
FIG. 3 is a structural schematic diagram of the occlusion device connected to the adjusting rod of the present disclosure.

Preferably, as shown in FIG. 3, the protrusion 311 is arranged on the inner side of each of the two clamping jaws 31 of the adjusting rod 3. The groove 211 is arranged at the protruding portion 21 of the adjusting device 2, and the protrusion 311 is engaged with the groove when the adjusting rod 3 is connected to the occlusion device 1, so as to increase the strength of the connection.

Preferably, the protrusion 311 in each of the two clamping jaws 31 is provided with a first magnet 34, and the groove 211 of the adjusting device 2 is provided with a second magnet 35, wherein the polarity of the first magnet 34 is opposite to the polarity of the second magnet 35. The two clamping jaws 31 of the adjusting rod 3 are tightly clamped on the protruding portion 21 of the adjusting device 2 of the occlusion device 1 by a magnetic attraction of the protrusion 311 and the groove 211. The occlusion device 1 is fixed at the interventricular septum to preliminarily fix the artificial chordae tendineae. When the length of the artificial chordae tendineae needs to be adjusted again, the adjusting rod 3 needs to be connected to the adjusting device 2 of the occlusion device 1 again. The magnetic attraction of the protrusion 311 and the groove 211 allows the adjusting rod 3 to be quickly connected to the occlusion device 1, which saves the time that the doctor spends in finding the connection point during the surgery, and facilitates repeatedly adjusting the artificial chordae tendineae.

Embodiment 3

Figure 4A:
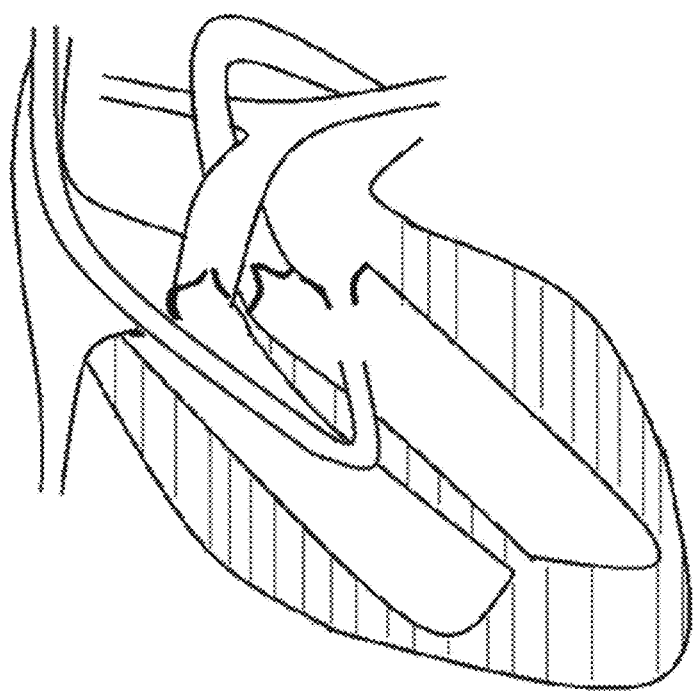
FIGS. 4A-4C form a flow chart showing the implanting method for the artificial chordae tendineae fixing assembly of the present disclosure.
Figure 4B:
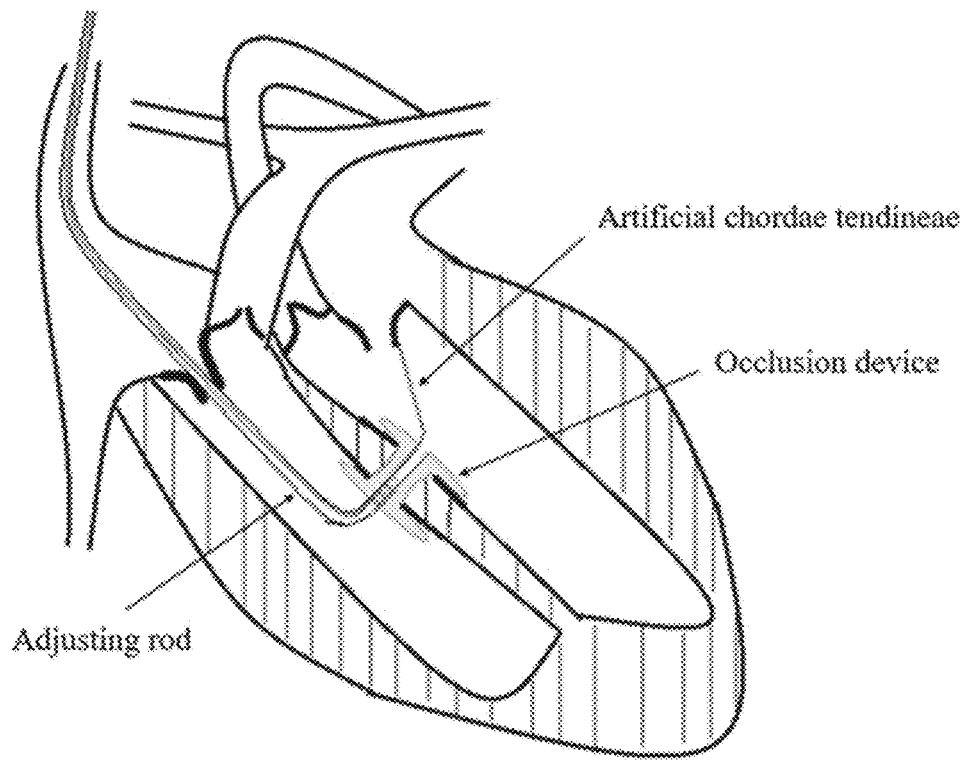
Figure 4C:
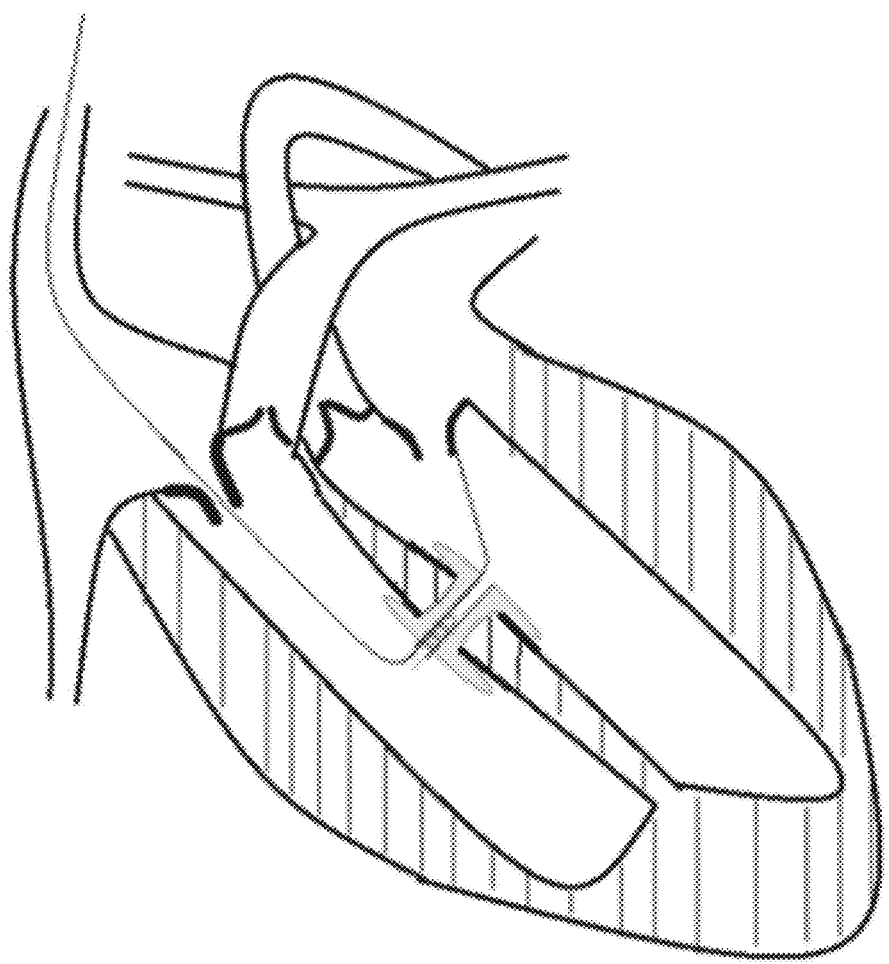

FIG. 4 is a flow chart showing the implanting method for the artificial chordae tendineae fixing assembly of the present disclosure. As shown in FIG. 4, the implanting method for the artificial chordae tendineae fixing assembly includes the following steps:

Step 1, the puncture sheath catheter penetrates the interventricular septum; the artificial chordae tendineae is inserted into a free margin of a diseased mitral leaflet through the perforation of the interventricular septum; and the tail of the artificial chordae tendineae is pulled out through the tail of the puncture sheath catheter.

Step 2, the adjusting rod 3 is connected to the adjusting device 2 of the occlusion device 1; the adjusting rod 3 is rotated to open the plurality of friction plates 23 of the adjusting device 2; wherein the artificial chordae tendineae penetrates into the occlusion device 1 and the adjusting rod 3 by using a traction pin 5, enters the penetrating passage from one side of the second occlusion disc 13, and is pulled out from the tail of the adjusting rod 3.

Step 3, the occlusion device 1 and the adjusting rod 3 are delivered along the puncture sheath catheter; the second occlusion disc 13 of the occlusion device is released on the left ventricular side of the interventricular septum; the waist portion 12 of the occlusion device 1 is placed in the perforation of the interventricular septum; the first occlusion disc 11 of the occlusion device 1 is released on the right ventricular side of the interventricular septum; the occlusion device 1 is clamped on the interventricular septum; the artificial chordae tendineae outside the tail of the adjusting rod 3 is pushed and pulled to adjust the length of the artificial chordae tendineae; and the plurality of friction plates 23 of the adjusting device 2 are closed to fix the artificial chordae tendineae.

Step 4, the handle at the tail of the adjusting rod 3 is pressed to open the two clamping jaws 31 at the head of the adjusting rod 3; the occlusion device 1 is released; the adjusting rod 3 is withdrawn; and the artificial chordae tendineae is retained outside a sheath catheter at a jugular venipuncture.

Step 5, the thread trimmer 4 is delivered along the tail of the artificial chordae tendineae; the handle at the tail of the thread trimmer 4 is triggered to cut off the artificial chordae tendineae after the thread trimmer reaches the occlusion device; the thread trimmer 4 is withdrawn; and the hemostasis is performed by a compression.

Preferably, step 4a may be included between step 4 and step 5, and step 4a includes: the artificial chordae tendineae is inserted into the adjusting rod 3 when the length of the artificial chordae tendineae is unsuitable due to a removal of anesthesia, a change in a cardiac volume, or other factors; the adjusting rod 3 is delivered to the outer side of the first occlusion disc 11 along the artificial chordae tendineae; the handle 32 at the tail of the adjusting rod 3 is pressed to clamp the two clamping jaws 31 of the adjusting rod 3 outside the protruding portion 21 of the adjusting device 2; the adjusting device 2 is rotated to allow the plurality of friction plates 23 to open the gap; the artificial chordae tendineae is loosened to readjust the length of the artificial chordae tendineae; then, the adjusting rod 3 is rotated to close the plurality of friction plates 23 of the adjusting device 2; the artificial chordae tendineae is fixed; the adjusting rod 3 is separated from the occlusion device 1; and the adjusting rod 3 is withdrawn from the body.

Figure 6:
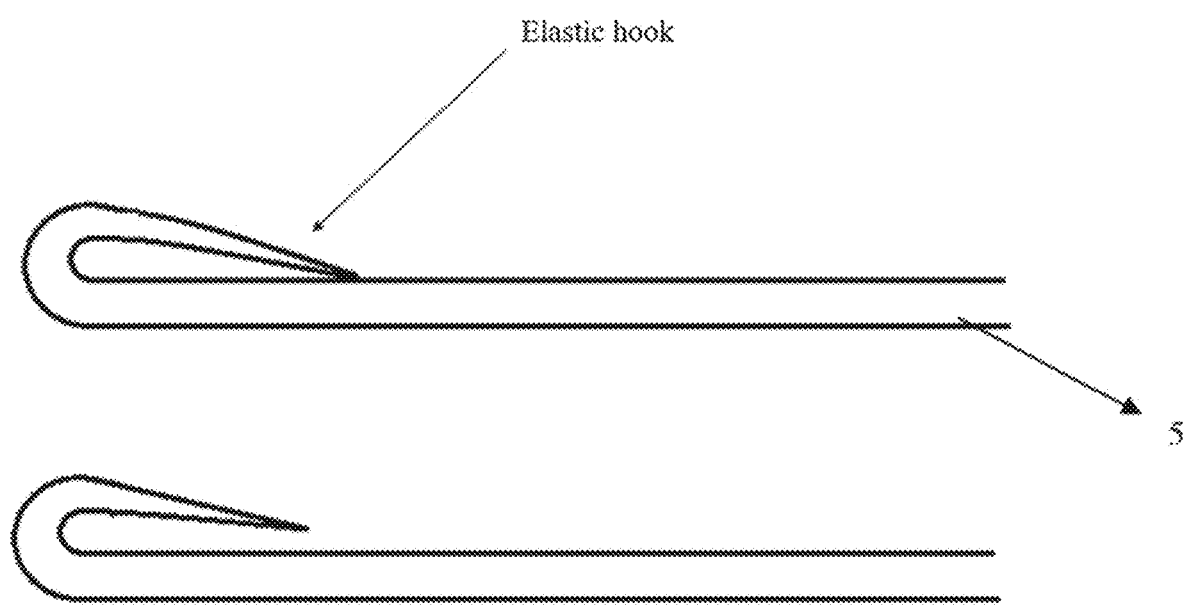
FIG. 6 is a structural schematic diagram of the traction pin of the present disclosure.
Figure 7A:
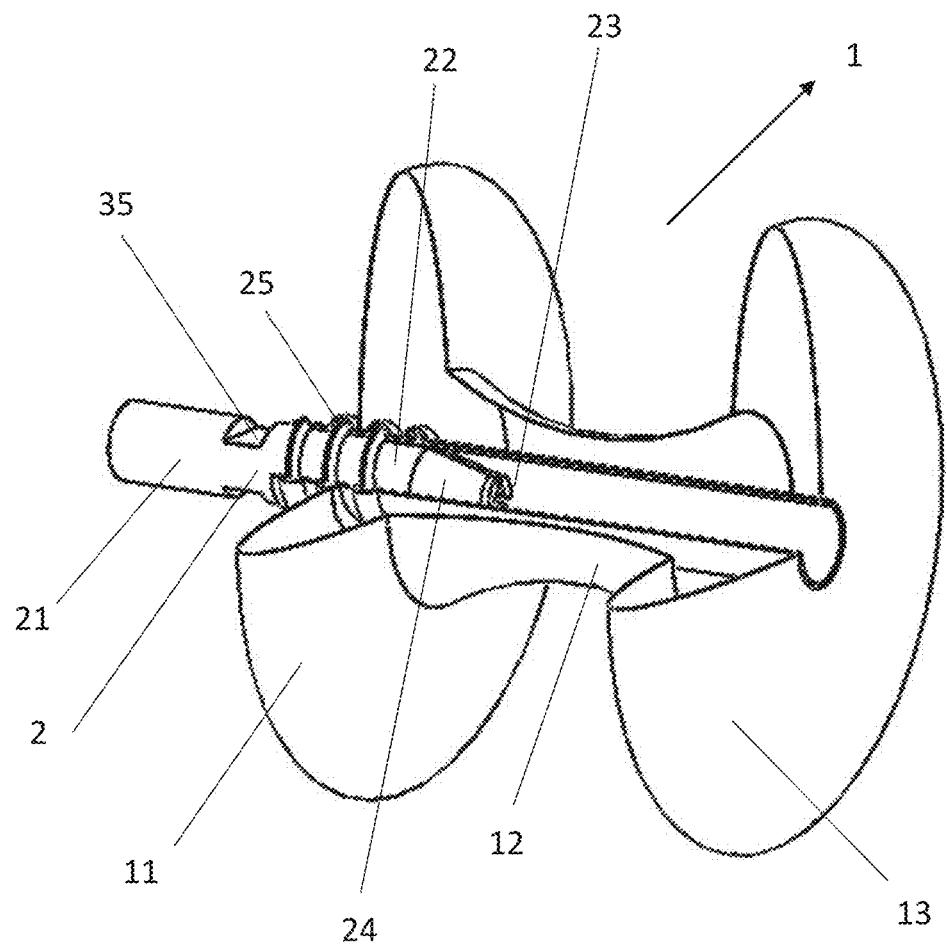
FIGS. 7A-7B are sectional views of FIG. 1.
Figure 7B:
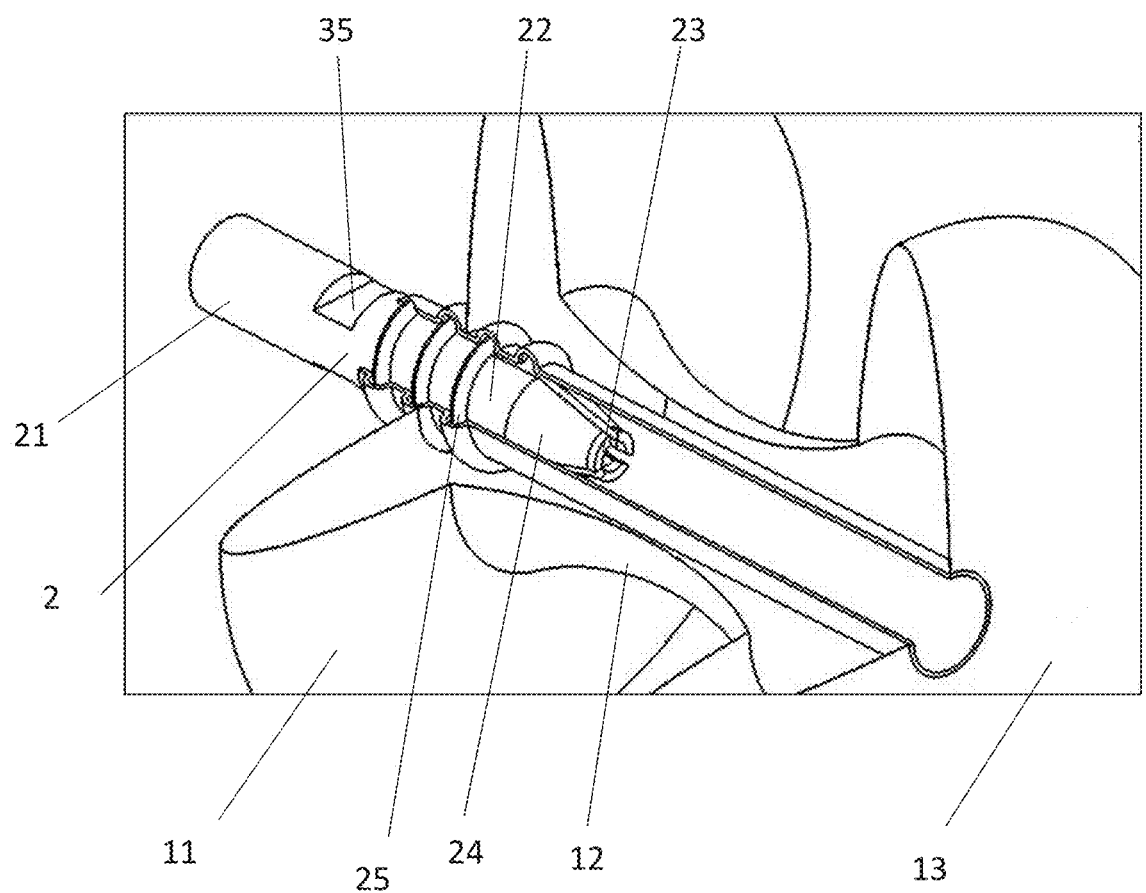

In step 1, after the tail of the artificial chordae tendineae is pulled out of the body, the artificial chordae tendineae is hooked by a traction pin 5, so as to insert the artificial chordae tendineae into the fixing assembly. The structure of the traction pin 5 is shown in FIG. 6, and the traction pin 5 is a rod-shaped structure. The head of the traction pin 5 is provided with a curved elastic hook, and the head of the elastic hook contacts the rod body of the traction pin 5 when the elastic hook is not in a strained condition. When the artificial chordae tendineae passes through the head of the elastic hook, the elastic hook is forced to open, so as to allow the artificial chordae tendineae to enter the inside of the elastic hook. After that, the head of the elastic hook is restored to contact the rod body, and the artificial chordae tendineae is placed inside the elastic hook, so as to hook the upper end of the artificial chordae tendineae.

Figure 5:
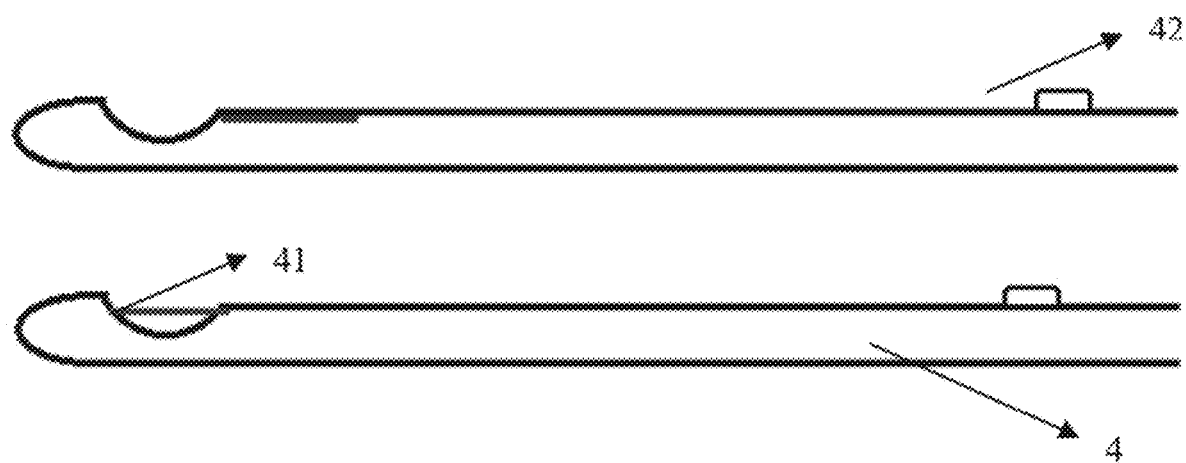
FIG. 5 is a structural schematic diagram of the thread trimmer of the present disclosure.

The present disclosure further provides a thread trimmer, as shown in FIG. 5. In step 5, the thread trimmer 4 is delivered along the tail of the artificial chordae tendineae through the puncture sheath catheter. The thread trimmer 4 is a rod-shaped structure, a thread trimming end and a handle end are provided at two ends of the thread trimmer, respectively. The thread trimming end is provided with a groove and the blade 41 capable of moving up and down along the groove. The handle end is provided with the push button 42, wherein the push button 42 is connected to the blade 41 inside the thread trimmer, and the blade 41 is controlled to move by the push button 42.

According to the present disclosure, the artificial chordae tendineae fixing assembly can fix the artificial chordae tendineae on the interventricular septum, and can also overcome the problem of unsuitable length of the artificial chordae tendineae due to cardiac changes occurring in most of patients after the procedure. The artificial chordae tendineae is retained at the skin puncture point for a short time. The length of the artificial chordae tendineae is adjusted again according to a cardiac change of the patient in an early postoperative period, thereby realizing the function of repeatedly adjusting the artificial chordae tendineae.

The above-mentioned embodiments are only intended to illustrate the embodiments of the present disclosure and thus are described in detail, which cannot be construed as a limitation on the scope of protection of the present disclosure. It should be noted that, those having ordinary skill in the art can make various modifications and improvements without departing from the concept of the present disclosure, and these modifications and improvements shall fall within the scope of protection of the present disclosure. Therefore, the scope of protection of the present disclosure is subject to the appended claims.

What is claimed is:

1. An adjustable artificial chordae tendineae fixing assembly, comprising:
   an occlusion device, and
   an adjusting rod;
   wherein
   the occlusion device comprises a first occlusion disc, a waist portion and a second occlusion disc;
   a middle of the first occlusion disc, a middle of the waist portion and a middle of the second occlusion disc of the occlusion device form a hollow passage allowing an artificial chordae tendineae to pass through;
   an adjusting device is arranged at an opening of the hollow passage in the first occlusion disc to limit a movement of the artificial chordae tendineae; wherein a protruding portion on an outer side of the adjusting device is arranged outside the first occlusion disc;
   a locking assembly and a plurality of friction plates on an inner side of the adjusting device extend inside an opening of the hollow passage; the locking assembly of the adjusting device is a threaded structure, and comprises a core and a ring; the core is connected to the plurality of friction plates; a number of the plurality of friction plates is at least two;
   the plurality of friction plates are controlled to open and close by rotation of the ring, wherein the plurality of friction plates are configured to clamp the artificial chordae tendineae when the plurality of friction plates are closed and are configured to allow the artificial chordae tendineae to pass therethrough when the plurality of friction plates are open;

the occlusion device is an elastic mesh structure configured to produce an elastic deformation; and the adjusting rod is a hollow rod-shaped structure allowing the artificial chordae tendineae to pass through; two clamping jaws are arranged at a head of the adjusting rod; the two clamping jaws are connected to a handle at a tail of the adjusting rod by a spring; the two clamping jaws are controlled to be opened and closed by pressing the handle at the tail of the adjusting rod; the two clamping jaws are clamped on the protruding portion of the adjusting device to be connected to the occlusion device;

wherein a protrusion is arranged on an inner side of each of the two clamping jaws of the adjusting rod; a groove is arranged at the protruding portion of the adjusting device; and the protrusion is engaged with the groove when the adjusting rod is connected to the occlusion device; and the two clamping jaws of the adjusting rod are clamped on the protruding portion of the adjusting device of the occlusion device by a magnetic attraction of the protrusion and the groove wherein the clamping jaws are configured to apply rotation to the ring to open and close the plurality of friction plates when the clamping jaws are clamped on the protruding portion.

2. The adjustable artificial chordae tendineae fixing assembly according to claim 1, wherein, the protrusion in each of the two clamping jaws is provided with a first magnet, and the groove of the adjusting device is provided with a second magnet, wherein a polarity of the first magnet is opposite to a polarity of the second magnet.

3. The adjustable artificial chordae tendineae fixing assembly according to claim 1, wherein, the occlusion device is woven from a nickel-titanium alloy wire; a diameter of the waist portion is 3 to 10 mm; a height of the waist portion is 2 to 20 mm; and a diameter of the first occlusion disc and a diameter of the second occlusion disc are both 7 to 28 mm.

4. The adjustable artificial chordae tendineae fixing assembly according to claim 3, wherein, the diameter of the waist portion is 6 mm; the height of the waist portion is 8 mm; the diameter of the first occlusion disc and the diameter of the second occlusion disc are both 10 mm.

* * * * *